United States Patent
Okada (10) Patent No.: US 9,952,521 B2
(45) Date of Patent: Apr. 24, 2018

(54) NAPHTHALENEDICARBOXIMIDE DERIVATIVE AND ELECTROPHOTOGRAPHIC PHOTOSENSITIVE MEMBER

(71) Applicant: KYOCERA Document Solutions Inc., Osaka (JP)

(72) Inventor: Hideki Okada, Osaka (JP)

(73) Assignee: KYOCERA Document Solutions Inc., Osaka (JP)

( * ) Notice: Subject to any disclaimer, the term of this patent is extended or adjusted under 35 U.S.C. 154(b) by 1 day.

(21) Appl. No.: 15/360,190

(22) Filed: Nov. 23, 2016

(65) Prior Publication Data

US 2017/0153560 A1  Jun. 1, 2017

(30) Foreign Application Priority Data

Nov. 30, 2015 (JP) .................. 2015-233062

(51) Int. Cl.
*G03G 5/06* (2006.01)
*C07D 221/18* (2006.01)
*G03G 5/047* (2006.01)

(52) U.S. Cl.
CPC ......... *G03G 5/0637* (2013.01); *C07D 221/18* (2013.01); *G03G 5/047* (2013.01); *G03G 5/0696* (2013.01)

(58) Field of Classification Search
CPC .... G03G 5/0637; G03G 5/047; C07D 221/18; C07D 221/16; C07D 221/06
USPC .................................................. 430/58.5, 78
See application file for complete search history.

(56) References Cited

U.S. PATENT DOCUMENTS

| | | | |
|---|---|---|---|
| 4,988,592 A * | 1/1991 | Sakamoto | C07D 221/14 430/59.1 |
| 7,291,429 B2 | 11/2007 | Kim et al. | |
| 2005/0112482 A1 | 5/2005 | Kim et al. | |
| 2011/0183462 A1* | 7/2011 | Shukla | H01L 51/0053 438/99 |

FOREIGN PATENT DOCUMENTS

JP  2005-154444 A  6/2005

OTHER PUBLICATIONS

Duan et al., Tetrahedron Letters (2009), vol. 50(1), pp. 22-25.*

* cited by examiner

*Primary Examiner* — Janis L Dote
(74) *Attorney, Agent, or Firm* — Studebaker & Brackett PC (57) ABSTRACT

A naphthalenedicarboximide derivative is represented by general formula (1) or (2). In general formulas (1) and (2), $R_1$, $R_2$, and $R_3$ each represent, independently of one another, an alkyl group which has a carbon number from 1 to 10 and which may have an aryl group having a carbon number from 6 to 14, an aryl group which has a carbon number from 6 to 14 and which may have an alkyl group having a carbon number from 1 to 10, a cycloalkyl group having a carbon number from 3 to 10, or an alkoxy group having a carbon number from 1 to 6, and m represents an integer from 0 to 4. When m represents an integer of 2 or more, chemical groups $R_2$ may each be the same or may each be different.

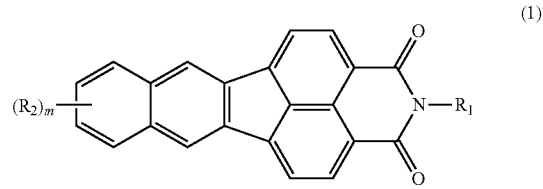

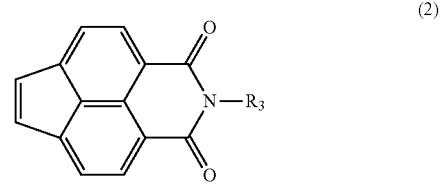

6 Claims, 4 Drawing Sheets

NAPHTHALENEDICARBOXIMIDE DERIVATIVE AND ELECTROPHOTOGRAPHIC PHOTOSENSITIVE MEMBER

INCORPORATION BY REFERENCE

The present application claims priority under 35 U.S.C. § 119 to Japanese Patent Application No. 2015-233062, filed on Nov. 30, 2015. The contents of this application are incorporated herein by reference in their entirety.

BACKGROUND

The present disclosure relates to a naphthalenedicarboximide derivative and an electrophotographic photosensitive member.

The electrophotographic photosensitive member is used for an electrophotographic image forming apparatus. The electrophotographic photosensitive member includes a photosensitive layer. For example, a multi-layer electrophotographic photosensitive member or a single-layer electrophotographic photosensitive member is used as the electrophotographic photosensitive member. The multi-layer electrophotographic photosensitive member includes, as the photosensitive layer, a charge generating layer having a charge generating function and a charge transport layer having a charge transporting function. The single-layer electrophotographic photosensitive member includes, as the photosensitive layer, a single-layer type photosensitive layer having the charge generating function and the charge transporting function.

The electrophotographic photosensitive member includes a conductive substrate and the photosensitive layer. The photosensitive layer for example contains a compound represented by chemical formula (E-1) shown below.

(E-1)

SUMMARY

A naphthalenedicarboximide derivative of the present disclosure is represented by general formula (1) or (2) shown below.

(1)

(2)

In the general formulas (1) and (2), $R_1$, $R_2$, and $R_3$ each represent, independently of one another, an alkyl group which has a carbon number of at least 1 and no greater than 10 and which may have an aryl group having a carbon number of at least 6 and no greater than 14, an aryl group which has a carbon number of at least 6 and no greater than 14 and which may have an alkyl group having a carbon number of at least 1 and no greater than 10, a cycloalkyl group having a carbon number of at least 3 and no greater than 10, or an alkoxy group having a carbon number of at least 1 and no greater than 6, and m represents an integer from 0 to 4. When m represents an integer of 2 or more, chemical groups $R_2$ may each be the same or may each be different.

An electrophotographic photosensitive member of the present disclosure includes a photosensitive layer. The photosensitive layer contains the above-described naphthalenedicarboximide derivative.

DETAILED DESCRIPTION

The following explains embodiments of the present disclosure in detail. However, the present disclosure is in no way limited to the embodiments. Appropriate variations may be made in practice within the intended scope of the present disclosure. Although explanation is omitted in some places in order to avoid repetition, such omission does not limit the essence of the present disclosure.

In the present description, the term "-based" may be appended to the name of a chemical compound in order to form a generic name encompassing both the chemical compound itself and derivatives thereof. Also, when the term "-based" is appended to the name of a chemical compound used in the name of a polymer, the term indicates that a repeating unit of the polymer originates from the chemical compound or a derivative thereof.

In the following description, a halogen atom, an alkyl group having a carbon number of at least 1 and no greater than 10, an alkyl group having a carbon number of at least 1 and no greater than 6, an alkyl group having a carbon number of at least 1 and no greater than 3, an alkyl group having a carbon number of at least 5 and no greater than 10, an alkoxy group having a carbon number of at least 1 and no greater than 6, an aryl group having a carbon number of at least 6 and no greater than 14, and a cycloalkyl group having a carbon number of at least 3 and no greater than 10 indicate the followings unless otherwise stated.

Examples of halogen atoms include a fluorine atom, a chlorine atom, and a bromine atom.

The alkyl group having a carbon number of at least 1 and no greater than 10 is an unsubstituted straight chain or branched chain alkyl group. Examples of alkyl groups having a carbon number of at least 1 and no greater than 10 include methyl group, ethyl group, n-propyl group, isopropyl group, n-butyl group, s-butyl group, t-butyl group, pentyl group, isopentyl group, neopentyl group, n-hexyl group, n-heptyl group, n-octyl group, 2-ethylhexyl group, n-nonyl group, and n-decyl group.

The alkyl group having a carbon number of at least 1 and no greater than 6 is an unsubstituted straight chain or branched chain alkyl group. Examples of alkyl groups having a carbon number of at least 1 and no greater than 6 include methyl group, ethyl group, n-propyl group, isopropyl group, n-butyl group, s-butyl group, t-butyl group, pentyl group, isopentyl group, neopentyl group, and hexyl group.

The alkyl group having a carbon number of at least 1 and no greater than 3 is an unsubstituted straight chain or branched chain alkyl group. Examples of alkyl groups having a carbon number of at least 1 and no greater than 3 include methyl group, ethyl group, n-propyl group, and isopropyl group.

The alkyl group having a carbon number of at least 5 and no greater than 10 is an unsubstituted straight chain or branched chain alkyl group. Examples of alkyl groups having a carbon number of at least 5 and no greater than 10 include pentyl group, isopentyl group, neopentyl group, n-hexyl group, n-heptyl group, n-octyl group, 2-ethylhexyl group, n-nonyl group, and n-decyl group.

The alkoxy group having a carbon number of at least 1 and no greater than 6 is an unsubstituted straight chain or branched chain alkoxy group. Examples of alkoxy groups having a carbon number of at least 1 and no greater than 6 include methoxy group, ethoxy group, n-propoxy group, isopropoxy group, n-butoxy group, s-butoxy group, t-butoxy group, pentyloxy group, isopentyloxy group, neopentyloxy group, and hexyloxy group.

Examples of aryl groups having a carbon number of at least 6 and no greater than 14 include unsubstituted monocyclic aromatic hydrocarbon groups having a carbon number of at least 6 and no greater than 14, unsubstituted condensed bicyclic aromatic hydrocarbon groups having a carbon number of at least 6 and no greater than 14, and unsubstituted condensed tricyclic aromatic hydrocarbon groups having a carbon number of at least 6 and no greater than 14. Specific examples of aryl groups having a carbon number of at least 6 and no greater than 14 include phenyl group, naphthyl group, anthryl group, and phenanthryl group.

The cycloalkyl group having a carbon number of at least 3 and no greater than 10 is an unsubstituted cycloalkyl group. Examples of cycloalkyl groups having a carbon number of at least 3 and no greater than 10 include cyclopropyl group, cyclobutyl group, cyclopentyl group, cyclohexyl group, cycloheptyl group, cyclooctyl group, cyclononyl group, and cyclodecyl group.

First Embodiment: Naphthalenedicarboximide Derivative

The first embodiment of the present disclosure is a naphthalenedicarboximide derivative. The naphthalenedicarboximide derivative of the first embodiment is represented by general formula (1) or (2) shown below.

(1)

(2)

In general formulas (1) and (2), $R_1$, $R_2$, and $R_3$ each represent, independently of one another, an alkyl group which has a carbon number of at least 1 and no greater than 10 and which may have an aryl group having a carbon number of at least 6 and no greater than 14, an aryl group which has a carbon number of at least 6 and no greater than 14 and which may have an alkyl group having a carbon number of at least 1 and no greater than 10, a cycloalkyl group having a carbon number of at least 3 and no greater than 10, or an alkoxy group having a carbon number of at least 1 and no greater than 6. In general formula (1), m represents an integer from 0 to 4. When m represents an integer of 2 or more, chemical groups $R_2$ may each be the same or may each be different.

In the case where the naphthalenedicarboximide derivatives represented by general formulas (1) and (2) (also referred to below as naphthalenedicarboximide derivatives (1) and (2)) are each contained in a photosensitive layer of an electrophotographic photosensitive member (also referred to below as a photosensitive member), the naphthalenedicarboximide derivatives (1) and (2) can improve electrical characteristics of the photosensitive member. The reason for the improvement of electrical characteristics of the photosensitive member is thought to be as follows.

The naphthalenedicarboximide derivatives (1) and (2) have a plane structure in which a condensed aromatic ring moiety (more specifically, a benzofluoranthene moiety or a naphthalene moiety) is bonded to an imide moiety. Thus, the naphthalenedicarboximide derivatives (1) and (2) have an asymmetric structure. Further, the naphthalenedicarboximide derivatives (1) and (2) have a structure in which the imide moiety is substituted with $R_1$ or $R_3$. The naphthalenedicarboximide derivatives (1) and (2), which have the above-described structure, easily dissolve in a solvent for photosensitive layer formation, and have excellent compatibility with a binder resin. Therefore, the naphthalenedicarboximide derivatives (1) and (2) are easily dispersed in the photosensitive layer in a uniform manner. It is thought that as a result of the above, carrier mobility in the photosensitive layer is improved, leading to an improvement of electrical characteristics (e.g., sensitivity characteristics) of the photosensitive member.

Further, the naphthalenedicarboximide derivatives (1) and (2), which have the above-described plane structure, have a relatively large π conjugated system. Therefore, the naphthalenedicarboximide derivatives (1) and (2) tend to give excellent electron acceptability or excellent electron mobility. It is thought that as a result of the above, carrier mobility in the photosensitive layer is improved, leading to the improvement of electrical characteristics of the photosensitive member.

The alkyl group which has a carbon number of at least 1 and no greater than 10 and which is represented by $R_1$ and $R_3$ in general formulas (1) and (2) is preferably an alkyl group having a carbon number of at least 5 and no greater than 10, more preferably an octyl group, and further preferably an n-octyl group or a 2-ethylhexyl group. The naphthalenedicarboximide derivatives (1) and (2) having the above-described alkyl group tend to have improved solubility in the solvent for photosensitive layer formation and improved compatibility with the binder resin while having the relatively large π conjugated system. The alkyl group which has a carbon number of at least 1 and no greater than 10 and which is represented by $R_2$ in general formula (1) is preferably an alkyl group having a carbon number of at least 1 and no greater than 6, more preferably an alkyl group having a carbon number of at least 1 and no greater than 3, and further preferably an ethyl group.

The alkyl group which has a carbon number of at least 1 and no greater than 10 and which is represented by $R_1$ and $R_3$ in general formulas (1) and (2) may have a substituent. The substituent is preferably an aryl group having a carbon number of at least 6 and no greater than 14, for example. Examples of the alkyl group which has a carbon number of at least 1 and no greater than 10 and an aryl group having a carbon number of at least 6 and no greater than 14 include an alkyl group which has a carbon number of at least 1 and no greater than 6 and a phenyl group (specific examples include a 4-phenyl-2-butyl group).

The aryl group which has a carbon number of at least 6 and no greater than 14 and which is represented by $R_1$, $R_2$, and $R_3$ in general formulas (1) and (2) may have a substituent. Examples of the substituent include a halogen atom, an alkyl group having a carbon number of at least 1 and no greater than 10, an alkoxy group having a carbon number of at least 1 and no greater than 6, and an aryl group having a carbon number of at least 6 and no greater than 14. Among the above substituents, the alkyl group having a carbon number of at least 1 and no greater than 10 is preferable.

$R_1$ and $R_3$ in general formulas (1) and (2) preferably each represent an alkyl group having a carbon number of at least 5 and no greater than 10, or an alkyl group which has a carbon number of at least 1 and no greater than 6 and an aryl group having a carbon number of at least 6 and no greater than 14 (specific examples include a phenyl group). It is thought that in the case where $R_1$ and $R_3$ each represent an alkyl group which has a carbon number of at least 1 and no greater than 6 and an aryl group having a carbon number of at least 6 and no greater than 14, and the binder resin has an aryl moiety (e.g., a benzene ring), the naphthalenedicarboximide derivative (1) or (2) and the binder resin tend to form a stacking structure in the photosensitive layer, leading to an improvement of compatibility of the naphthalenedicarboximide derivative (1) or (2) with the binder resin. It is thought that as a result of the above, the naphthalenedicarboximide derivative (1) or (2) uniformly disperses in the photosensitive layer, leading to the improvement of electrical characteristics of the photosensitive member. From the viewpoint of the improvement of electrical characteristics of the photosensitive member, $R_2$ preferably represents an alkyl group having a carbon number of at least 1 and no greater than 3. Also, m preferably represents 0 or 1, and more preferably represents 1. It is thought that in the case where m represents 1 and $R_2$ represents an alkyl group having a carbon number of at least 1 and no greater than 3, molecules of the naphthalenedicarboximide derivative (1) are easily entangled with molecules of the binder resin, leading to the improvement of the compatibility of the naphthalenedicarboximide derivative (1) with the binder resin. It is thought that as a result of the above, the naphthalenedicarboximide derivative (1) uniformly disperses in the photosensitive layer, leading to the improvement of electrical characteristics of the photosensitive member.

Specific examples of the naphthalenedicarboximide derivative (1) include naphthalenedicarboximide derivatives represented by chemical formulas (1-1) to (1-4) shown below (also referred to below as naphthalenedicarboximide derivatives (1-1) to (1-4)). In chemical formulas (1-1) and (1-4), n-$C_8H_{17}$ represents an n-octyl group.

(1-1)

(1-2)

(1-3)

(1-4)

Specific examples of the naphthalenedicarboximide derivative (2) include naphthalenedicarboximide derivatives represented by chemical formulas (2-1) to (2-3) shown below (also referred to below as naphthalenedicarboximide derivatives (2-1) to (2-3)). In chemical formula (2-1), n-$C_8H_{17}$ represents an n-octyl group.

(2-1)

(2-2)

(2-3)

The naphthalenedicarboximide derivative (1) is produced, for example, by a reaction represented by reaction formula (R-1) shown below (also referred to below as reaction (R-1)) or through a method in accordance with the aforementioned reaction formula. In addition to the above reaction, other processes may be carried out as appropriate depending on necessity thereof.

$R_1$, $R_2$, and m in reaction formula (R-1) represent the same as $R_1$, $R_2$, and m in general formula (1), respectively.

In the reaction (R-1), 1 equivalent of a compound represented by general formula (A) (also referred to below as compound (A)) is caused to react with 1 equivalent of a compound represented by general formula (B) (also referred to below as compound (B)) in a solvent in the presence of a reductant to yield 1 equivalent of the naphthalenedicarboximide derivative (1). In the reaction (R-1), at least 1 mol and no greater than 2.5 mol of the compound (B) is preferably added relative to 1 mol of the compound (A). If at least 1 mol of the compound (B) is added relative to 1 mol of the compound (A), a percentage yield of the naphthalenedicarboximide derivative (1) can be easily improved. If no greater than 2.5 mol of the compound (B) is added relative to 1 mol of the compound (A), the compound (B) is prevented from being left unreacted after the reaction, so that the naphthalenedicarboximide derivative (1) can be easily purified. A reaction temperature of the reaction (R-1) is preferably at least 50° C. and no greater than 150° C. The reaction (R-1) preferably has a reaction time of at least 10 hours and no greater than 30 hours. The reaction (R-1) may be conducted in a solvent. Examples of solvents that can be used include dimethyl formamide (DMF) and dimethyl sulfoxide (DMSO). Examples of reductants that can be used include potassium iodide and sodium iodide.

Through the above, an explanation of the naphthalenedicarboximide derivative according to the first embodiment has been provided. The naphthalenedicarboximide derivative according to the first embodiment can improve electrical characteristics of the photosensitive member.

Second Embodiment: Photosensitive Member

The second embodiment relates to a photosensitive member. The photosensitive member may be a multi-layer photosensitive member or a single-layer photosensitive member. The photosensitive member includes a conductive substrate and a photosensitive layer. The photosensitive layer contains the naphthalenedicarboximide derivative (1) or (2).

<1. Multi-Layer Photosensitive Member>

Figure 1A:
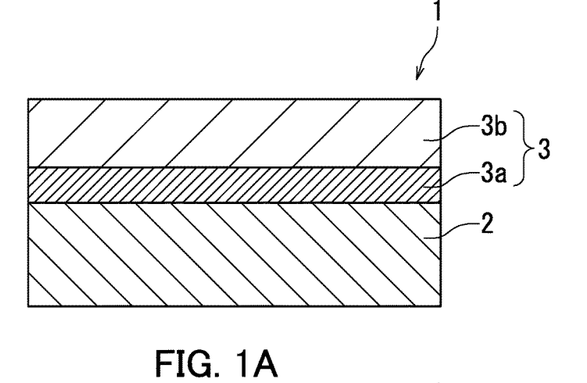
FIGS. 1A to 1C are schematic cross sectional views each illustrating an example of an electrophotographic photosensitive member according to a second embodiment of the present disclosure.
Figure 1B:
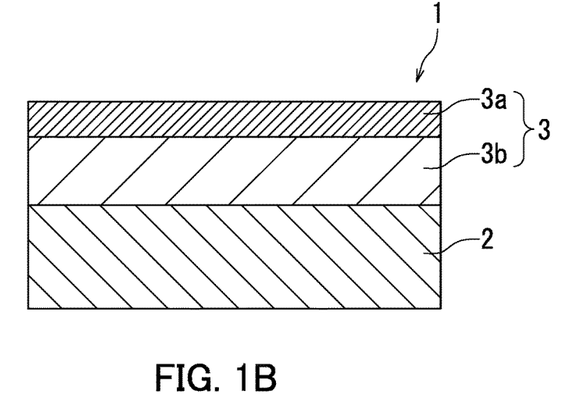
Figure 1C:
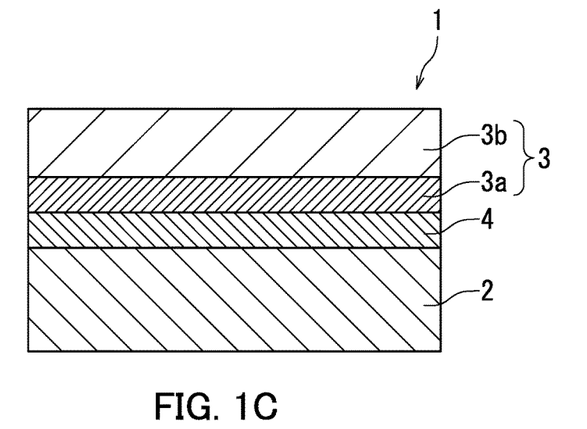

The following explains a structure of a photosensitive member 1 in the case where the photosensitive member 1 is a multi-layer photosensitive member with reference to FIGS. 1A to 1C. FIGS. 1A to 1C are schematic cross-sectional views each illustrating an example of the photosensitive member 1 according to the second embodiment in the form of the multi-layer photosensitive member.

As illustrated in FIG. 1A, the multi-layer photosensitive member includes a conductive substrate 2 and a photosensitive layer 3. The photosensitive layer 3 includes a charge generating layer 3a and a charge transport layer 3b. In order to improve abrasion resistance of the multi-layer photosensitive member, it is preferable that the charge generating layer 3a is located on the conductive substrate 2 and the charge transport layer 3b is located on the charge generating layer 3a, as illustrated in FIG. 1A.

As illustrated in FIG. 1B, in the multi-layer photosensitive member as the photosensitive member 1, the charge transport layer 3b may be located on the conductive substrate 2, and the charge generating layer 3a may be located on the charge transport layer 3b.

As illustrated in FIG. 1C, the multi-layer photosensitive member as the photosensitive member 1 may include the conductive substrate 2, the photosensitive layer 3, and an intermediate layer (underlayer) 4. The intermediate layer 4 is provided between the conductive substrate 2 and the photosensitive layer 3. Further, a protective layer 5 may be provided on the photosensitive layer 3 (see FIG. 2C).

No specific limitations are placed on the thicknesses of the charge generating layer 3a and the charge transport layer 3b, so long as the thicknesses thereof are sufficient to enable the charge generating layer 3a and the charge transport layer 3b to implement their respective functions. The thickness of the charge generating layer 3a is preferably at least 0.01 μm and no greater than 5 μm, and more preferably at least 0.1 μm and no greater than 3 μm. The thickness of the charge transport layer 3b is preferably at least 2 μm and no greater than 100 μm, and more preferably at least 5 μm and no greater than 50 μm.

The charge generating layer 3a in the photosensitive layer 3 contains a charge generating material. The charge generating layer 3a may contain a charge generating layer binder resin (also referred to below as a base resin). The charge generating layer 3a may contain, as needed, various additives.

The charge transport layer 3b contains the naphthalenedicarboximide derivative (1) or (2) as an electron-accepting compound. The charge transport layer 3b may contain a hole transport material or a binder resin. The charge transport layer 3b may contain, as needed, various additives. Through the above, an explanation of the structure of the photosensitive member 1 in the form of the multi-layer photosensitive member has been provided with reference to FIGS. 1A to 1C.

<2. Single-Layer Photosensitive Member>

Figure 2A:
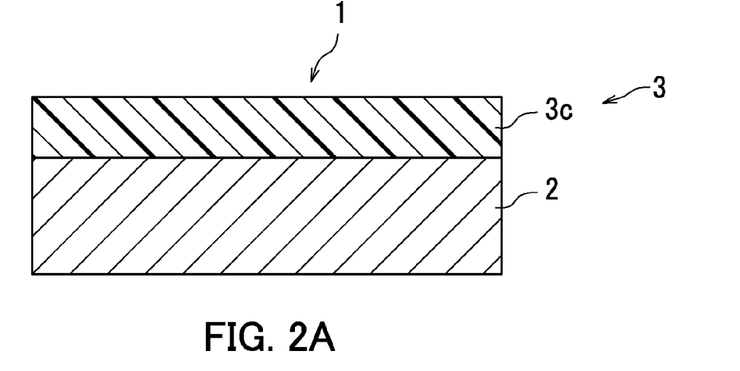
FIGS. 2A to 2C are schematic cross sectional views each illustrating another example of the electrophotographic photosensitive member according to the second embodiment of the present disclosure.
Figure 2B:
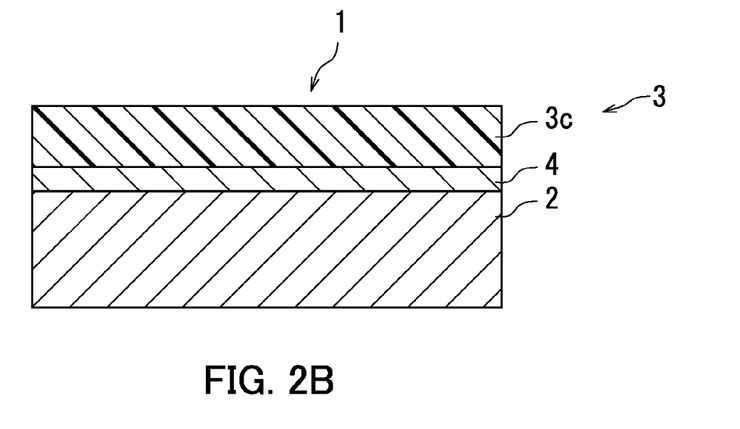
Figure 2C:
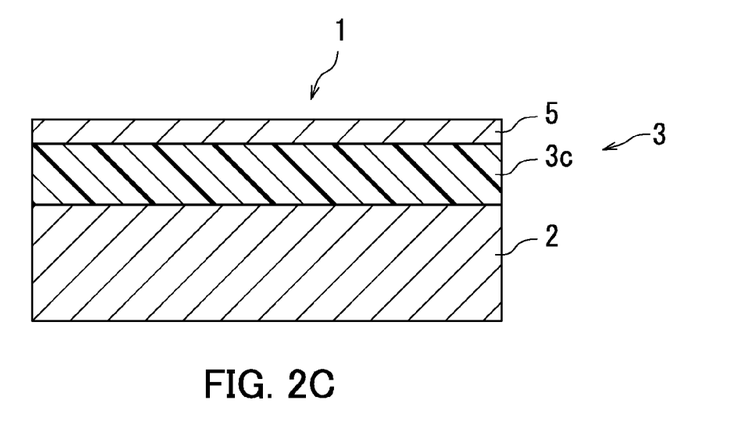

The following explains a structure of the photosensitive member 1 in the case where the photosensitive member 1 is a single-layer photosensitive member with reference to FIGS. 2A to 2C. FIGS. 2A to 2C are schematic cross-sectional views each illustrating another example of the photosensitive member 1 according to the present embodiment in the form of the single-layer photosensitive member.

As illustrated in FIG. 2A, the single-layer photosensitive member as the photosensitive member 1 includes for example the conductive substrate 2 and the photosensitive layer 3. The single-layer photosensitive member as the photosensitive member 1 includes a single-layer type photosensitive layer 3c as the photosensitive layer 3. The single-layer type photosensitive layer 3c is a photosensitive layer 3 having a single layer.

As illustrated in FIG. 2B, the single-layer photosensitive member as the photosensitive member 1 may include the conductive substrate 2, the single-layer type photosensitive layer 3c, and the intermediate layer (underlayer) 4. The intermediate layer 4 is provided between the conductive substrate 2 and the single-layer type photosensitive layer 3c. Further, the protective layer 5 may be provided on the single-layer type photosensitive layer 3c, as illustrated in FIG. 2C.

No specific limitations are placed on the thickness of the single-layer type photosensitive layer 3c, so long as the thickness thereof is sufficient to enable the single-layer type photosensitive layer 3c to function as a single-layer type photosensitive layer. The thickness of the single-layer type photosensitive layer 3c is preferably at least 5 μm and no greater than 100 μm, and more preferably at least 10 μm and no greater than 50 μm.

The single-layer type photosensitive layer 3c as the photosensitive layer 3 contains the naphthalenedicarboximide derivative (1) or (2) as an electron transport material. The single-layer type photosensitive layer 3c may further contain at least one of the charge generating material, the hole transport material, and the binder resin. The single-layer type photosensitive layer 3c may contain, as needed, various additives. That is, in the case where the photosensitive member 1 is the single-layer photosensitive member, the electron transport material and optionally added components (the charge generating material, the hole transport material, the binder resin, the additives or the like) are contained in the photosensitive layer 3 having a single layer (single-layer type photosensitive layer 3c). Through the above, an explanation of the structure of the photosensitive member 1 in the form of the single-layer photosensitive member has been provided with reference to FIGS. 2A to 2C.

Next, elements of the multi-layer photosensitive member and the single-layer photosensitive member will be explained.

<3. Conductive Substrate>

No specific limitations are placed on the conductive substrate other than being a conductive substrate that can be used in a photosensitive member. It is sufficient that at least a surface portion of the conductive substrate is made of a conductive material. An example of the conductive substrate is a conductive substrate made of a conductive material. Another example of the conductive substrate is a conductive substrate having a conductive material coating. Examples of conductive materials that can be used include aluminum, iron, copper, tin, platinum, silver, vanadium, molybdenum, chromium, cadmium, titanium, nickel, palladium, and indium. Any one of the conductive materials listed above may be used or a combination of any two or more of the conductive materials listed above may be used. Examples of combinations of two or more of the conductive materials include alloys (specific examples include aluminum alloys, stainless steel, and brass). Among the conductive materials listed above, aluminum or an aluminum alloy is preferable in terms of favorable charge mobility from the photosensitive layer to the conductive substrate.

The shape of the conductive substrate is selected as appropriate to match with the structure of an image forming apparatus in which the conductive substrate is to be used. The conductive substrate takes the form of a sheet or a drum, for example. The thickness of the conductive substrate is selected as appropriate in accordance with the shape of the conductive substrate.

<4. Naphthalenedicarboximide Derivative>

The photosensitive layer contains the naphthalenedicarboximide derivative (1) or (2) according to the first embodiment. In the case of the multi-layer photosensitive member, the charge transport layer contains the naphthalenedicarboximide derivative (1) or (2) as the electron acceptor compound. In the case of the single-layer photosensitive member, the single-layer type photosensitive layer contains the naphthalenedicarboximide derivative (1) or (2) as the electron transport material. In the case where the photosensitive layer contains the naphthalenedicarboximide derivative (1) or (2), electrical characteristics of the photosensitive member can be improved as described above with respect to the first embodiment.

In the case of the multi-layer photosensitive member, the amount of the naphthalenedicarboximide derivative (1) or (2) is preferably at least 10 parts by mass and no greater than 200 parts by mass with respect to 100 parts by mass of the binder resin contained in the charge transport layer, and more preferably at least 20 parts by mass and no greater than 100 parts by mass.

In the case of the single-layer photosensitive member, the amount of the naphthalenedicarboximide derivative (1) or (2) is preferably at least 10 parts by mass and no greater than 200 parts by mass with respect to 100 parts by mass of the binder resin contained in the single-layer type photosensitive layer, more preferably at least 10 parts by mass and no greater than 100 parts by mass, and particularly preferably at least 10 parts by mass and no greater than 75 parts by mass.

The charge transport layer may contain the naphthalenedicarboximide derivatives (1) and (2). The charge transport layer may further contain another electron acceptor compound in addition to the naphthalenedicarboximide derivative (1) or (2). The single-layer type photosensitive layer may further contain another electron transport material in addition to the naphthalenedicarboximide derivative (1) or (2). Examples of other electron acceptor compounds and other electron transport materials that can be used include quinone-based compounds, diimide-based compounds, hydrazone-based compounds, malononitrile-based compounds, thiopyran-based compounds, trinitrothioxanthone-based compounds, 3,4,5,7-tetranitro-9-fluorenone-based compounds, dinitroanthracene-based compounds, dinitroacridine-based compounds, tetracyanoethylene, 2,4,8-trinitrothioxanthone, dinitrobenzene, dinitroacridine, succinic anhydride, maleic anhydride, and dibromomaleic anhydride. Examples of quinone-based compounds that can be used include diphenoquinone-based compounds, azoquinone-based compounds, anthraquinone-based compounds, naphthoquinone-based compounds, nitroanthraquinone-based compounds, and dinitroanthraquinone-based compounds. Any one of the electron acceptor compounds and electron transport materials listed above may be used or a combination of any two or more of the electron acceptor compounds and electron transport materials listed above may be used.

<5. Hole Transport Material>

In the case of the multi-layer photosensitive member, the charge transport layer may contain the hole transport material. In the case of the single-layer photosensitive member, the single-layer type photosensitive layer may contain the hole transport material. Examples of hole transport materials that can be used include nitrogen containing cyclic compounds and condensed polycyclic compounds. Examples of nitrogen containing cyclic compounds and condensed polycyclic compounds that can be used include diamine derivatives (specific examples include N,N,N',N'-tetraphenylphenylenediamine derivatives, N,N,N',N'-tetraphenylnaphtylenediamine derivatives, and N,N,N',N'-tetraphenylphenanthrylenediamine derivatives), oxadiazole-based compounds (specific examples include 2,5-di(4-methylaminophenyl)-1,3,4-oxadiazole), styryl compounds (specific examples include 9-(4-diethylaminostyryl)anthracene), carbazole compounds (specific examples include polyvinyl carbazole), organic polysilane compounds, pyrazoline-based compounds (specific examples include 1-phenyl-3-(p-dimethylaminophenyl)pyrazoline), hydrazone-based compounds, indole-based compounds, oxazole-based compounds, isoxazole-based compounds, thiazole-based compounds, thiadiazole-based compounds, imidazole-based compounds, pyrazole-based compounds, and triazole-based compounds. Any one of the hole transport materials listed above may be used or a combination of any two or more of the hole transport materials listed above may be used. Among the hole transport materials listed above, a compound represented by chemical formula (HT-1) shown below (also referred to below as compound (HT-1)) is preferable.

(HT-1)

In the case of the multi-layer photosensitive member, the amount of the hole transport material is preferably at least 10 parts by mass and no greater than 200 parts by mass with respect to 100 parts by mass of the binder resin contained in the charge transport layer, and more preferably at least 20 parts by mass and no greater than 100 parts by mass.

In the case of the single-layer photosensitive member, the amount of the hole transport material is preferably at least 10 parts by mass and no greater than 200 parts by mass with respect to 100 parts by mass of the binder resin contained in the single-layer type photosensitive layer, more preferably at least 10 parts by mass and no greater than 100 parts by mass, and particularly preferably at least 10 parts by mass and no greater than 75 parts by mass.

<6. Charge Generating Material>

In the case of the multi-layer photosensitive member, the charge generating layer may contain the charge generating material. In the case of the single-layer photosensitive member, the single-layer type photosensitive layer may contain the charge generating material.

No specific limitations are placed on the charge generating material other than being a charge generating material that can be used in a photosensitive member. Examples of charge generating materials that can be used include phthalocyanine-based pigments, perylene-based pigments, bisazo pigments, tris-azo pigments, dithioketopyrrolopyrrole pigments, metal-free naphthalocyanine pigments, metal naphthalocyanine pigments, squaraine pigments, indigo pigments, azulenium pigments, cyanine pigments, powders of inorganic photoconductive materials (specific examples include selenium, selenium-tellurium, selenium-arsenic, cadmium sulfide, and amorphous silicon), pyrylium pigments, anthanthrone-based pigments, triphenylmethane-based pigments, threne-based pigments, toluidine-based pigments, pyrazoline-based pigments, and quinacridone-based pigments. Any one of the charge generating materials listed above may be used or a combination of any two or more of the charge generating materials listed above may be used.

Examples of phthalocyanine-based pigments that can be used include metal-free phthalocyanine represented by chemical formula (C-1) shown below (also referred to below as compound (C-1)) and metal phthalocyanines. Examples of metal phthalocyanines that can be used include titanyl phthalocyanine represented by chemical formula (C-2) shown below (also referred to below as compound (C-2)), hydroxygallium phthalocyanine, and chlorogallium phthalocyanine. The phthalocyanine-based pigments may be crystalline or non-crystalline. No specific limitations are placed on the crystal structure (e.g., α-form, β-form, Y-form, V-form, or II-form) of the phthalocyanine-based pigments, and the phthalocyanine-based pigments having various crystal structures may be used.

(C-1)

(C-2)

An example of crystalline metal-free phthalocyanine is metal-free phthalocyanine having an X-form crystal structure (also referred to below as X-form metal-free phthalocyanine). An example of crystalline titanyl phthalocyanine is titanyl phthalocyanine having an α-form, β-form, or Y-form crystal structure (also referred to below as α-form, β-form, or Y-form titanyl phthalocyanine). An example of crystalline hydroxygallium phthalocyanine is hydroxygallium phthalocyanine having a V-form crystal structure. An example of crystalline chlorogallium phthalocyanine is chlorogallium phthalocyanine having a II-form crystal structure.

For image forming apparatuses employing, for example, a digital optical system, a photosensitive member having a sensitivity in a wavelength range of 700 nm or longer is preferred. Examples of image forming apparatuses employing the digital optical system include a laser beam printer or facsimile machine that uses a light source such as a semiconductor laser. As the charge generating material, the phthalocyanine-based pigments are preferable, and the metal-free phthalocyanine and titanyl phthalocyanine are more preferable in terms of their high quantum yield in the wavelength range of 700 nm or longer. In order to further improve electrical characteristics of the photosensitive member in the case where the photosensitive layer contains the naphthalenedicarboximide derivative, the charge generating material is further preferably the X-form metal-free phthalocyanine or the Y-form titanyl phthalocyanine.

The Y-form titanyl phthalocyanine exhibits a main peak, for example, at a Bragg angle (2θ±0.2°) of 27.2° in a CuKα characteristic X-ray diffraction spectrum. The term main peak in the CuKα characteristic X-ray diffraction spectrum refers to a most intense or second most intense peak within a range of Bragg angles (2θ±0.2°) from 3° to 40°.

(Method for Measuring CuKα Characteristic X-Ray Diffraction Spectrum)

The following explains an example of a method for measuring the CuKα characteristic X-ray diffraction spectrum. A sample (titanyl phthalocyanine) is loaded into a sample holder of an X-ray diffraction spectrometer (e.g., RINT (registered Japanese trademark) 1100 produced by Rigaku Corporation) and an X-ray diffraction spectrum is measured using a Cu X-ray tube, a tube voltage of 40 kV, a tube current of 30 mA, and X-rays characteristic of CuKα having a wavelength of 1.542 Å. The measurement range (2θ) is, for example, from 3° to 40° (start angle: 3°, stop angle: 40°) and the scanning speed is, for example, 10°/minute.

For the photosensitive member included in image forming apparatuses including a short-wavelength laser light source, the anthanthrone-based pigments are preferably used as the charge generating material. The wavelength of short-wavelength laser light is, for example, at least 350 nm and no greater than 550 nm.

In the case of the multi-layer photosensitive member, the amount of the charge generating material is preferably at least 5 parts by mass and no greater than 1,000 parts by mass with respect to 100 parts by mass of the base resin contained in the charge generating layer, and more preferably at least 30 parts by mass and no greater than 500 parts by mass.

In the case of the single-layer photosensitive member, the amount of the charge generating material is preferably at least 0.1 part by mass and no greater than 50 parts by mass with respect to 100 parts by mass of the binder resin contained in the single-layer type photosensitive layer, more preferably at least 0.5 part by mass and no greater than 30 parts by mass, and particularly preferably at least 0.5 part by mass and no greater than 4.5 parts by mass.

<7. Binder Resin>

In the case of the multi-layer photosensitive member, the charge transport layer may contain the binder resin. In the case of the single-layer photosensitive member, the single-layer type photosensitive layer may contain the binder resin.

Examples of binder resins that can be used include thermoplastic resins, thermosetting resins, and photocurable resins. Examples of thermoplastic resins that can be used include polycarbonate resins, polyarylate resins, styrene-butadiene resins, styrene-acrylonitrile resins, styrene-maleic acid resins, acrylic acid-based resins, styrene-acrylic acid-based resins, polyethylene resins, ethylene-vinyl acetate resins, chlorinated polyethylene resins, polyvinyl chloride resins, polypropylene resins, ionomer resins, vinyl chloride-vinyl acetate resins, alkyd resins, polyamide resins, urethane resins, polysulfone resins, diallyl phthalate resins, ketone resins, polyvinyl butyral resins, polyester resins, and polyether resins. Examples of thermosetting resins that can be used include silicone resins, epoxy resins, phenolic resins, urea resins, and melamine resins. Examples of photocurable resins that can be used include epoxy-acrylic acid-based resins (specific examples include acrylic acid derivative adducts of epoxy compounds) and urethane-acrylic acid-based resins (specific examples include acrylic acid derivative adducts of urethane compounds). Any one of the binder resins listed above may be used or a combination of any two or more of the binder resins listed above may be used.

Among the resins listed above, the polycarbonate resins are favorable in terms of providing the single-layer type photosensitive layer and the charge transport layer having excellent balance of processability, mechanical strength, optical characteristics, and abrasion resistance. Examples of polycarbonate resins that can be used include bisphenol Z polycarbonate resins (also referred to below as Z-form polycarbonate resins (Resin-1)) represented by chemical formula (Resin-1) shown below, bisphenol ZC polycarbonate resins, bisphenol C polycarbonate resins, and bisphenol A polycarbonate resins.

(Resin-1)

The binder resin preferably has a viscosity average molecular weight of at least 40,000, and more preferably at least 40,000 and no greater than 52,500. As a result of the viscosity average molecular weight of the binder resin being at least 40,000, abrasion resistance of the photosensitive member can be improved more easily. As a result of the viscosity average molecular weight of the binder resin being no greater than 52,500, the binder resin dissolves more easily in a solvent in formation of the photosensitive layer and viscosity of an application liquid for charge transport layer formation or an application liquid for single-layer type photosensitive layer formation is not excessively high. Consequently, the charge transport layer or the single-layer type photosensitive layer can be formed more easily.

<8. Base Resin>

In the case of the multi-layer photosensitive member, the charge generating layer contains the base resin. No specific limitations are placed on the base resin other than being a base resin that can be used in a photosensitive member. Examples of base resins that can be used include thermoplastic resins, thermosetting resins, and photocurable resins. Examples of thermoplastic resins that can be used include styrene-butadiene resins, styrene-acrylonitrile resins, styrene-maleic acid resins, styrene-acrylic acid-based resins, acrylic acid-based resins, polyethylene resins, ethylene-vinyl acetate resins, chlorinated polyethylene resins, polyvinyl chloride resins, polypropylene resins, ionomers, vinyl chloride-vinyl acetate resins, alkyd resins, polyamide resins, urethane resins, polycarbonate resins, polyarylate resins, polysulfone resins, diallyl phthalate resins, ketone resins, polyvinyl butyral resins, polyether resins, and polyester resins. Examples of thermosetting resins that can be used include silicone resins, epoxy resins, phenolic resins, urea resins, melamine resins, and other crosslinkable thermosetting resins. Examples of photocurable resins that can be used include epoxy-acrylic acid-based resins (specific examples include acrylic acid derivative adducts of epoxy compounds) and urethane-acrylic acid-based resins (specific examples include acrylic acid derivative adducts of urethane compounds). Any one of the base resins listed above may be used or a combination of any two or more of the base resins listed above may be used.

The multi-layer photosensitive member is typically produced by forming the charge generating layer on the conductive substrate and forming the charge transport layer on the charge generating layer. The charge transport layer is formed by applying the application liquid for charge transport layer formation onto the charge generating layer. Therefore, it is preferable that the base resin contained in the charge generating layer differs from the binder resin contained in the charge transport layer to prevent the charge generating layer from dissolving in a solvent of the application liquid for charge transport layer formation.

<9. Additives>

The photosensitive layer (e.g., the charge generating layer, the charge transport layer, or the single-layer type photosensitive layer) of the photosensitive member may contain, as needed, various additives. Examples of additives that can be used include antidegradants (specific examples include antioxidants, radical scavengers, quenchers, and ultraviolet absorbing agents), softeners, surface modifiers, extenders, thickeners, dispersion stabilizers, waxes, donors, surfactants, plasticizers, sensitizers, and leveling agents. Examples of antioxidants that can be used include hindered phenols (specific examples include di(tert-butyl)p-cresol), hindered amines, paraphenylenediamine, arylalkanes, hydroquinone, spirochromanes, spiroindanones, derivatives of any of the above compounds, organosulfur compounds, and organophosphorus compounds.

<10. Intermediate Layer>

The intermediate layer (underlayer) contains for example inorganic particles and a resin (intermediate layer resin). It is thought that provision of the intermediate layer facilitates flow of current generated when the photosensitive member is exposed to light and inhibits increasing resistance, while also maintaining insulation to a sufficient degree so as to inhibit leakage current from occurring.

Examples of inorganic particles that can be used include particles of metals (specific examples include aluminum, iron, and copper), particles of metal oxides (specific examples include titanium oxide, alumina, zirconium oxide, tin oxide, and zinc oxide), and particles of non-metal oxides (specific examples include silica). Any one of the types of inorganic particles listed above may be used or a combination of any two or more of the types of inorganic particles listed above may be used.

No specific limitations are placed on the intermediate layer resin other than being a resin that can be used to form an intermediate layer. The intermediate layer may contain various additives. The additives that may be contained in the intermediate layer are the same as those that may be contained in the photosensitive layer.

<11. Method for Producing Photosensitive Member>

The multi-layer photosensitive member is produced as described below, for example. First, an application liquid for charge generating layer formation and an application liquid for charge transport layer formation are prepared. The application liquid for charge generating layer formation is applied onto a conductive substrate and dried thereon to form a charge generating layer. Subsequently, the application liquid for charge transport layer formation is applied onto the charge generating layer and dried thereon to form a charge transport layer. Thus, the multi-layer photosensitive member is produced.

The application liquid for charge generating layer formation is prepared by dissolving or dispersing a charge generating material and additive components (e.g., a base resin and various additives), depending on necessity thereof, in a solvent. The application liquid for charge transport layer formation is prepared by dissolving or dispersing an electron acceptor compound and additive components (e.g., a binder resin, a hole transport material, and various additives), depending on necessity thereof, in a solvent.

The single-layer photosensitive member is produced by applying an application liquid for single-layer type photosensitive layer formation onto a conductive substrate and drying the application liquid thereon. The application liquid for single-layer type photosensitive layer formation is prepared by dissolving or dispersing an electron transport material and additive components (e.g., a charge generating material, a hole transport material, a binder resin, and various additives), depending on necessity thereof, in a solvent.

No particular laminations are placed on the solvents contained in the application liquid for charge generating layer formation, the application liquid for charge transport layer formation, and the application liquid for single-layer type photosensitive layer formation (these three application liquids will be also referred to below as application liquids) other than that components of the application liquids should be soluble or dispersible in the solvents. Examples of solvents that can be used include alcohols (specific examples include methanol, ethanol, isopropanol, and butanol), aliphatic hydrocarbons (specific examples include n-hexane, octane, and cyclohexane), aromatic hydrocarbons (specific examples include benzene, toluene, and xylene), halogenated hydrocarbons (specific examples include dichloromethane, dichloroethane, carbon tetrachloride, and chlorobenzene), ethers (specific examples include dimethyl ether, diethyl ether, tetrahydrofuran, ethylene glycol dimethyl ether, diethylene glycol dimethyl ether, and propylene glycol monomethyl ether), ketones (specific examples include acetone, methyl ethyl ketone, and cyclohexanone), esters (specific examples include ethyl acetate and methyl acetate), dimethyl formaldehyde, dimethyl formamide, and dimethyl sulfoxide. Any one of the solvents listed above may be used or a combination of any two or more of the solvents listed above may be used. Use of a non-halogenated solvent (i.e., a solvent other than a halogenated hydrocarbon) is preferable in order to improve workability during production of the photosensitive member.

Each of the application liquids is prepared by mixing the components to disperse the components in the solvent. Mixing or dispersion can for example be performed using a bead mill, a roll mill, a ball mill, an attritor, a paint shaker, or an ultrasonic disperser.

Each of the application liquids may for example contain a surfactant in order to improve dispersibility of the components.

No specific limitations are placed on the method by which the application liquids are applied other than being a method that enables uniform application of the application liquids onto the conductive substrate. Examples of application methods that can be used include dip coating, spray coating, spin coating, and bar coating.

No specific limitations are placed on the method by which the application liquids are dried other than being a method that enables evaporation of the solvents contained in the application liquids. The method for drying the application liquids may for example be heat treatment (hot-air drying) using a high-temperature dryer or a reduced pressure dryer. The heat treatment is for example performed for at least 3 minutes and no greater than 120 minutes at a temperature of at least 40° C. and no greater than 150° C.

The method for producing the photosensitive member may further include either or both of a process for forming the intermediate layer and a process for forming the protective layer as necessary. The process for forming the intermediate layer and the process for forming the protective layer are carried out by methods selected appropriately from known methods.

Through the above, the photosensitive member according to the present embodiment has been explained. According to the photosensitive member of the present embodiment, electrical characteristics of the photosensitive member can be improved.

EXAMPLES

The following provides more specific explanation of the present disclosure through use of Examples. However, it should be noted that the present disclosure is not limited to the scope of the Examples.

<1. Materials of Photosensitive Member>

A hole transport material, charge generating materials, and electron transport materials described below were prepared as materials for forming single-layer type photosensitive layers of single-layer photosensitive members.

<1-1. Electron Transport Material>

Naphthalenedicarboximide derivatives (1-1) to (1-4) and (2-1) were prepared as electron transport materials. Among these naphthalenedicarboximide derivatives, the naphthalenedicarboximide derivatives (1-1) to (1-4) were produced by respective methods described below.

<1-1-1. Production of Naphthalenedicarboximide Derivative (1-1)>

The naphthalenedicarboximide derivative (1-1) was produced by a reaction represented by reaction formula (R-2) shown below (also referred to below as reaction (R-2)).

In the reaction (R-2), a compound (1A) was caused to react with a compound (1B) to yield the naphthalenedicarboximide derivative (1-1). Specifically, 0.33 g (1.00 mmol) of the compound (1A), 0.42 g (1.00 mmol) of the compound (1B), 0.5 g (3.00 mmol) of potassium iodide, and 50 mL of dimethyl formamide were added into a flask having a capacity of 200 mL. The flask contents were stirred for 24 hours at 80° C., and were subsequently cooled to room temperature. Ion exchanged water was added to the flask contents to extract an organic layer. The organic layer was evaporated under reduced pressure to leave a residue. The resultant residue was purified by silica gel chromatography, using chloroform as a developing solvent. Thus, the naphthalenedicarboximide derivative (1-1) was obtained. Mass yield of the naphthalenedicarboximide derivative (1-1) was 0.26 g and percentage yield of the naphthalenedicarboximide derivative (1-1) was 60 mol %.

<1-1-2. Production of Naphthalenedicarboximide Derivatives (1-2) to (1-4)>

The naphthalenedicarboximide derivatives (1-2) to (1-4) were produced by the same method as the naphthalenedicarboximide derivative (1-1) in all aspects other than the changes described below. Materials used in production of the naphthalenedicarboximide derivatives (1-2) to (1-4) were each added in the same number of moles as that of a corresponding one of the materials used in production of the naphthalenedicarboximide derivative (1-1).

Table 1 shows first materials, second materials, and reaction products in the reaction (R-2). The first materials and the second materials are reactants in the reaction (R-2). The compound (1A) used in the reaction (R-2) was changed to the first materials shown in Table 1, and the compound (1B) used in the reaction (R-2) was changed to the second materials shown in Table 1. As a result, the naphthalenedicarboximide derivatives (1-2) to (1-4) were obtained. Table 1 shows the mass yield and the percentage yield of the naphthalenedicarboximide derivatives (1).

In Table 1, "2A" and "3A" indicated in the "Compound" column of the first material represent a compound (2A) and a compound (3A), respectively. "2B" indicated in the "Compound" column of the second material represents a compound (2B). The compounds (2A), (3A), and (2B) are respectively represented by chemical formulas (2A), (3A), and (2B) shown below.

TABLE 1

| | Reaction (R-2) | | | | | | | |
|---|---|---|---|---|---|---|---|---|
| First material | | | Second material | | | Reaction product | | |
| Compound | Additive amount [g] | Additive amount [mmol] | Compound | Additive amount [g] | Additive amount [mmol] | Naphthalenedi- carboximide derivative | Mass yield [g] | Percentage yield [mol %] |
| 1A | 0.33 | 1.00 | 1B | 0.42 | 1.00 | 1-1 | 0.26 | 60 |
| 2A | 0.33 | 1.00 | 1B | 0.42 | 1.00 | 1-2 | 0.24 | 55 |
| 3A | 0.35 | 1.00 | 1B | 0.42 | 1.00 | 1-3 | 0.23 | 50 |
| 1A | 0.33 | 1.00 | 2B | 0.45 | 1.00 | 1-4 | 0.25 | 55 |

(2A)

(3A)

(2B)

Next, infrared absorption spectrums of the produced naphthalenedicarboximide derivatives (1-1) to (1-4) were measured using a Fourier transform infrared spectrophotometer (SPECTRUM ONE produced by PerkinElmer Co., Ltd.). Samples were prepared by KBr (potassium bromide) pellet method. The infrared absorption spectrums were used to confirm that the naphthalenedicarboximide derivatives (1-1) to (1-4) had been obtained. Among the naphthalenedicarboximide derivatives (1-1) to (1-4), the naphthalenedicarboximide derivatives (1-1) and (1-3) will be described below as representative examples.

Figure 3:
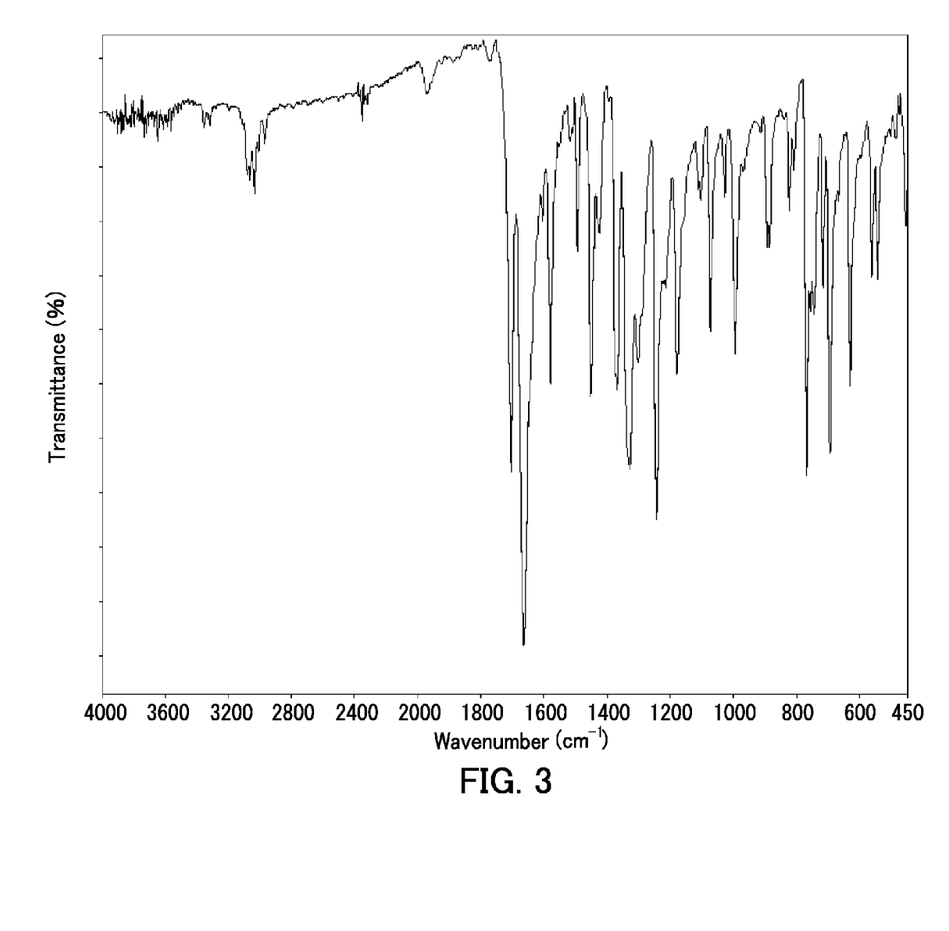
FIG. 3 illustrates an infrared absorption spectrum of a naphthalenedicarboximide derivative represented by chemical formula (1-1) according to a first embodiment of the present disclosure.
Figure 4:
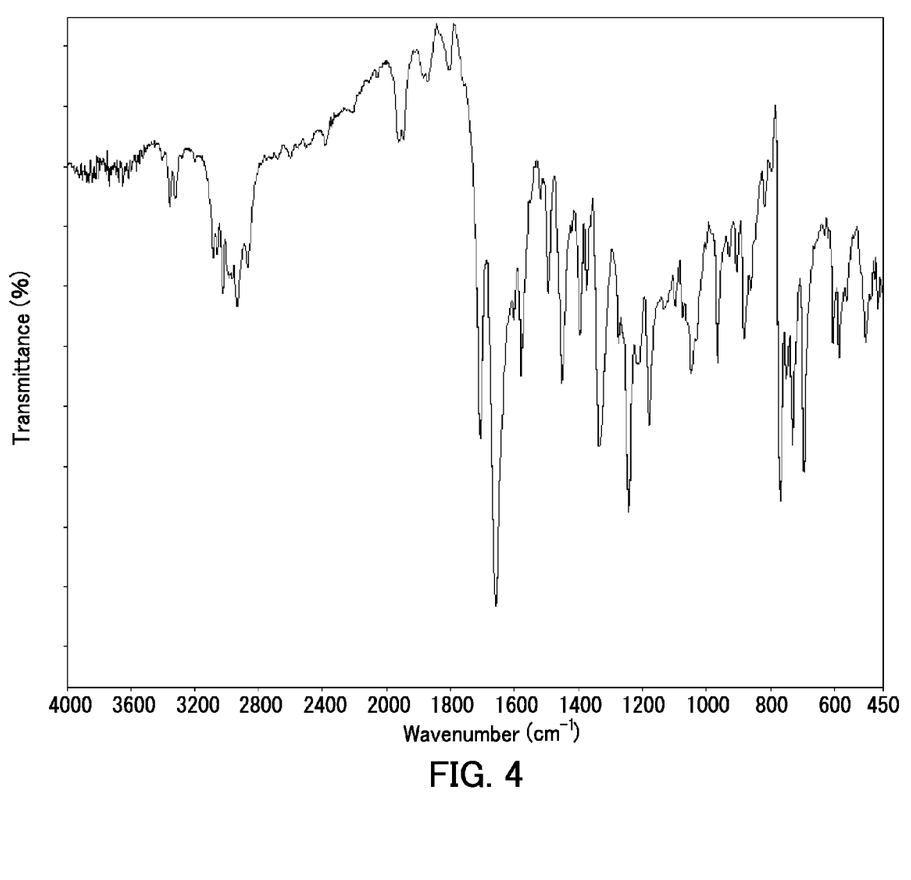
FIG. 4 illustrates an infrared absorption spectrum of a naphthalenedicarboximide derivative represented by chemical formula (1-3) according to the first embodiment of the present disclosure.

FIGS. 3 and 4 show the infrared absorption spectrums of the naphthalenedicarboximide derivatives (1-1) and (1-3), respectively. In FIGS. 3 and 4, the vertical axis represents transmittance and the horizontal axis represents wavenumber. The unit % of the vertical axis (transmittance) in FIGS. 3 and 4 is an arbitrary unit. Wavenumbers ($v_{MAX}$) at absorption peaks of the naphthalenedicarboximide derivatives (1-1) and (1-3) are shown below.

Naphthalenedicarboximide derivative (1-1): IRcm$^{-1}$: 3034, 1703, 1664, 1244

Naphthalenedicarboximide derivative (1-3): IRcm$^{-1}$: 3025, 1707, 1659, 1244

<1-1-3. Preparation of Compound (E-1)>

A compound represented by chemical formula (E-1) shown below (also referred to below as compound (E-1)) was prepared as an electron transport material.

(E-1)

<1-2. Hole Transport Material>

The compound (HT-1) explained above in the second embodiment was prepared as a hole transport material.

<1-3. Charge Generating Material>

Compounds (C-1) to (C-2) were prepared as charge generating materials. The compound (C-1) was metal-free phthalocyanine (X-form metal-free phthalocyanine) represented by chemical formula (C-1) explained above in the second embodiment. The crystal structure of the compound (C-1) was X-form.

The compound (C-2) was titanyl phthalocyanine (Y-form titanyl phthalocyanine) represented by chemical formula (C-2) explained above in the second embodiment. The crystal structure of the compound (C-2) was Y-form.

<1-4. Binder Resin>

The Z-form polycarbonate resin (Resin-1) (PANLITE (registered Japanese trademark) TS-2050 produced by Teijin Limited, viscosity average molecular weight 50,000) explained above in the second embodiment was prepared as a binder resin.

<2. Production of Single-Layer Photosensitive Member>

Single-layer photosensitive members (A-1) to (A-10) and (B-1) to (B-2) were produced using materials for photosensitive layer formation.

<2-1. Production of Single-Layer Photosensitive Member (A-1)>

First, 5 parts by mass of the compound (C-1) as the charge generating material, 80 parts by mass of the compound (HT-1) as the hole transport material, 40 parts by mass of the naphthalenedicarboximide derivative (1-1) as the electron transport material, 100 parts by mass of the Z-form polycarbonate resin (Resin-1) as the binder resin, and 800 parts by mass of tetrahydrofuran as a solvent were added into a container. The container contents were mixed for 50 hours using a ball mill in order to disperse the materials in the solvent. Through the above process, an application liquid for single-layer type photosensitive layer formation was prepared. The application liquid for single-layer type photosensitive layer formation was applied onto a conductive substrate—an aluminum drum-shaped support (diameter 30 mm, total length 238.5 mm)—by dip coating. The applied application liquid for single-layer type photosensitive layer formation was hot-air dried at 100° C. for 30 minutes. Thus, the single-layer type photosensitive layer (film thickness 30 μm) was formed on the conductive substrate. The single-layer photosensitive member (A-1) was obtained as a result of the process described above.

<2-2. Production of Single-Layer Photosensitive Members (A-2) to (A-10) and (B-1) to (B-2)>

The single-layer photosensitive members (A-2) to (A-10) and (B-1) to (B-2) were produced by the same method as the single-layer photosensitive member (A-1) in all aspects other than the changes described below. The compound (C-1) used as the charge generating material in production of the single-layer photosensitive member (A-1) was changed to charge generating materials shown in Table 2. The naphthalenedicarboximide derivative (1-1) used as the electron transport material in production of the single-layer photosensitive member (A-1) was changed to electron transport materials shown in Table 2. Table 2 shows compositions of the photosensitive members (A-1) to (A-10) and (B-1) to (B-2). In Table 2, "CGM", "HTM", and "ETM" represent the charge generating material, the hole transport material, and the electron transport material, respectively. In Table 2, "x-H$_2$Pc" and "Y-TiOPc" indicated in the "CGM" column represent the X-form metal-free phthalocyanine and the Y-form titanyl phthalocyanine, respectively. "HT-1" indicated in the "HTM" column represents the compound (HT-1). "1-1" to "1-4", "2-1", and "E-1" indicated in the "ETM" column represent the naphthalenedicarboximide derivatives (1-1) to (1-4) and (2-1), and the compound (E-1), respectively.

<3. Performance Evaluation of Photosensitive Member>

<3-1. Evaluation of Electrical Characteristics of Single-Layer Photosensitive Member>

Electrical characteristics of each of the produced single-layer photosensitive members (A-1) to (A-10) and (B-1) to (B-2) were evaluated. The electrical characteristics were evaluated in an environment at a temperature of 23° C. and a relative humidity of 60%. The surface of the single-layer photosensitive member was charged to a positive polarity using a drum sensitivity test device (produced by Gen-Tech, Inc.) by setting a rotation speed of the single-layer photosensitive member at 31 rpm and setting an electric current flowing into the single-layer photosensitive member at +8 μA. A surface potential of the single-layer photosensitive member immediately after the charging was set at +700 V. Next, a band pass filter was used to obtain monochromatic light (wavelength 780 nm, half-width 20 nm, light intensity 1.5 μJ/cm$^2$) from white light emitted by a halogen lamp. The surface of the single-layer photosensitive member was irradiated with the obtained monochromatic light. The surface potential of the single-layer photosensitive member was measured once 0.5 seconds had elapsed after completion of the irradiation. The measured surface potential was taken to be a sensitivity potential ($V_L$, units: V). Table 2 shows the measured sensitivity potential ($V_L$) of the single-layer photosensitive member. It should be noted that a sensitivity potential ($V_L$) having a smaller absolute value indicates better electrical characteristics of the single-layer photosensitive member.

<3-2. Evaluation of Inhibition of Crystallization of Photosensitive Member>

The surfaces of the produced single-layer photosensitive members (A-1) to (A-10) and (B-1) to (B-2) were visually observed.

TABLE 2

| Photosensitive member No | Photosensitive layer | | | Electrical characteristics |
| | CGM | HTM | ETM | $V_L(V)$ |
| --- | --- | --- | --- | --- |
| Example 1 | A-1 | x-H$_2$Pc | HT-1 | 1-1 | +108 |
| Example 2 | A-2 | Y—TiOPc | HT-1 | 1-1 | +102 |
| Example 3 | A-3 | x-H$_2$Pc | HT-1 | 1-2 | +107 |
| Example 4 | A-4 | Y—TiOPc | HT-1 | 1-2 | +102 |
| Example 5 | A-5 | x-H$_2$Pc | HT-1 | 1-3 | +106 |
| Example 6 | A-6 | Y—TiOPc | HT-1 | 1-3 | +102 |
| Example 7 | A-7 | x-H$_2$Pc | HT-1 | 1-4 | +103 |
| Example 8 | A-8 | Y—TiOPc | HT-1 | 1-4 | +99 |
| Example 9 | A-9 | x-H$_2$Pc | HT-1 | 2-1 | +110 |
| Example 10 | A-10 | Y—TiOPc | HT-1 | 2-1 | +107 |
| Comparative example 1 | B-1 | x-H$_2$Pc | HT-1 | E-1 | +135 |
| Comparative example 2 | B-2 | Y—TiOPc | HT-1 | E-1 | +130 |

As shown in Table 2, the photosensitive layers of the photosensitive members (A-1) to (A-10) each contained any one of the naphthalenedicarboximide derivatives (1-1) to (1-4) and (2-1) as the electron transport material. The naphthalenedicarboximide derivatives (1-1) to (1-4) and (2-1) were the naphthalenedicarboximide derivatives represented by general formula (1) or (2). The sensitivity potentials of the photosensitive members (A-1) to (A-10) were at least +99 V and no greater than +110 V.

As shown in Table 2, the photosensitive layers of the photosensitive members (B-1) to (B-2) contained the compound (E-1) as the electron transport material. The compound (E-1) was neither of the naphthalenedicarboximide derivatives (1) and (2). The sensitivity potentials of the photosensitive members (B-1) to (B-2) were at least +130 V and no greater than +135 V.

It is obvious that the photosensitive members (A-1) to (A-10) have better electrical characteristics than the photosensitive members (B-1) to (B-2).

The evaluation results indicate that in the case where the naphthalenedicarboximide derivative represented by general formula (1) or (2) is contained in the photosensitive layer, the naphthalenedicarboximide derivative improves electrical characteristics of the photosensitive member. Also, the evaluation results indicate that the photosensitive member including the photosensitive layer that contains the naphthalenedicarboximide derivative represented by general formula (1) or (2) has excellent electrical characteristics.

Further, crystallization was not observed at the surfaces of the photosensitive members (A-1) to (A-10). By contrast, slight crystallization was observed at the surfaces of the photosensitive members (B-1) to (B-2). The above indicates that in the case where the naphthalenedicarboximide derivative represented by general formula (1) or (2) is contained in the photosensitive layer, the naphthalenedicarboximide derivative inhibits crystallization at the surface of the photosensitive member. Also, the above indicates that crystallization is inhibited in the photosensitive member including the photosensitive layer that contains the naphthalenedicarboximide derivative represented by general formula (1) or (2).

What is claimed is:

1. A naphthalenedicarboximide derivative represented by general formula (1) or (2) shown below wherein in the general formulas (1) and (2),
R$_1$ and R$_3$ each represent, independently of one another, an alkyl group having a carbon number of at least 5 and no greater than 10 or an alkyl group which has a carbon number of at least 1 and no greater than 6 and which is substituted with a phenyl group,
R$_2$ represents an alkyl group having a carbon number of at least 1 and no greater than 3, and
m represents 0 or 1.

2. The naphthalenedicarboximide derivative according to claim 1, wherein in the general formulas (1) and (2),
R$_1$ and R$_3$ each represent an alkyl group which has a carbon number of at least 1 and no greater than 6 and which is substituted with a phenyl group.

3. The naphthalenedicarboximide derivative according to claim 1,
represented by chemical formula (1-1), (1-2), (1-3), (1-4), or (2-1) shown below 4. An electrophotographic photosensitive member, comprising
a conductive substrate and a photosensitive layer,
wherein the photosensitive layer contains the naphthalenedicarboximide derivative according to claim 1.

5. The electrophotographic photosensitive member according to claim 4, wherein
the photosensitive layer is a single-layer photosensitive layer having a single layer,
the single-layer photosensitive layer further contains a charge generating material, and
the charge generating material includes X-form metal-free phthalocyanine or Y-form titanyl phthalocyanine.

6. The electrophotographic photosensitive member according to claim 4, wherein
the photosensitive layer further contains a hole transport material, and
the hole transport material includes a compound represented by chemical formula (HT-1) shown below (HT-1)

* * * * *